(12) United States Patent
Meskens (10) Patent No.: US 10,201,704 B2
(45) Date of Patent: Feb. 12, 2019

(54) DIGITAL COMMUNICATIONS IN AN IMPLANTABLE SYSTEM

(71) Applicant: Cochlear Limited, Macquarie University, NSW (AU)

(72) Inventor: Werner Meskens, Opwijk (BE)

(73) Assignee: Cochlear Limited, Macquarie University (AU)

( * ) Notice: Subject to any disclaimer, the term of this patent is extended or adjusted under 35 U.S.C. 154(b) by 272 days.

(21) Appl. No.: 15/045,582

(22) Filed: Feb. 17, 2016

(65) Prior Publication Data

US 2016/0243363 A1 Aug. 25, 2016

Related U.S. Application Data

(60) Provisional application No. 62/118,490, filed on Feb. 20, 2015.

(51) Int. Cl.
| | | |
|---|---|---|
| *A61N 1/00* | (2006.01) | |
| *A61N 1/36* | (2006.01) | |
| *A61N 1/372* | (2006.01) | |

(52) U.S. Cl.
CPC ..... *A61N 1/36036* (2017.08); *A61N 1/37252* (2013.01)

(58) Field of Classification Search
CPC ............ A61N 1/36032; A61N 1/36036; A61N 1/37252
See application file for complete search history.

(56) References Cited

U.S. PATENT DOCUMENTS

| | | | | |
|---|---|---|---|---|
| 4,459,989 | A * | 7/1984 | Borkan | .................. A61N 1/372 451/533 |
| 5,704,351 | A * | 1/1998 | Mortara | ............... A61B 5/0006 128/904 |
| 7,139,613 | B2 | 11/2006 | Reinke et al. | |
| 2010/0114258 | A1* | 5/2010 | Donofrio | .................. A61N 1/37 607/63 |
| 2012/0116479 | A1 | 5/2012 | Meskins et al. | |

\* cited by examiner

*Primary Examiner* — Lindsey G Wehrheim
(74) *Attorney, Agent, or Firm* — Edell, Shapiro & Finnan, LLC (57) ABSTRACT

Presented herein are implantable digital communication techniques for use in implantable systems, such as implantable hearing systems. An implantable system in accordance with embodiments presented herein includes an implantable stimulator module and an implantable secondary module connected to the implantable stimulator module via a wire connection. The implantable secondary module is configured to generate and send a biphasic information signal to the implantable stimulator module via the wire connection. An error detector in the implantable stimulator module is configured to detect when the biphasic information signal includes an error.

20 Claims, 9 Drawing Sheets

DIGITAL COMMUNICATIONS IN AN IMPLANTABLE SYSTEM

CROSS-REFERENCE TO RELATED APPLICATIONS

This application claims priority to U.S. Provisional Application No. 62/118,490 entitled "Digital Communications in an Implantable System," filed Feb. 20, 2015, the content of which is hereby incorporated by reference herein.

BACKGROUND

Field of the Invention

The present invention relates generally to a digital audio link in an implantable hearing system.

Related Art

Hearing loss, which may be due to many different causes, is generally of two types, conductive and/or sensorineural. Conductive hearing loss occurs when the normal mechanical pathways of the outer and/or middle ear are impeded, for example, by damage to the ossicular chain or ear canal. Sensorineural hearing loss occurs when there is damage to the inner ear, or to the nerve pathways from the inner ear to the brain.

Individuals who suffer from conductive hearing loss typically have some form of residual hearing because the hair cells in the cochlea are undamaged. As such, individuals suffering from conductive hearing loss typically receive an auditory prosthesis that generates motion of the cochlea fluid. Such auditory prostheses include, for example, acoustic hearing aids, bone conduction devices, and direct acoustic stimulators.

In many people who are profoundly deaf, however, the reason for their deafness is sensorineural hearing loss. Those suffering from some forms of sensorineural hearing loss are unable to derive suitable benefit from auditory prostheses that generate mechanical motion of the cochlea fluid. Such individuals can benefit from implantable auditory prostheses that stimulate nerve cells of the recipient's auditory system in other ways (e.g., electrical, optical and the like). Cochlear implants are often proposed when the sensorineural hearing loss is due to the absence or destruction of the cochlea hair cells, which transduce acoustic signals into nerve impulses. Auditory brainstem stimulators might also be proposed when a recipient experiences sensorineural hearing loss due to damage to the auditory nerve.

SUMMARY

In one aspect an implantable medical system is provided. The implantable medical system comprises an implantable stimulator module, an implantable secondary module connected to the implantable stimulator module via a wire connection, wherein the implantable secondary module is configured to generate and send, to the implantable stimulator module via the wire connection, a biphasic information signal comprising a series of alternating positive and negative pulses, and an error detector in the implantable stimulator module configured to detect when the biphasic information signal includes an error.

In another aspect an implantable medical system is provided. The implantable medical system comprises an implantable stimulator module connected to an array of stimulation contacts to deliver stimulation signals to a recipient, an implantable secondary module comprising one or more sound input elements and configured to receive an alternating electrical power signal from the implantable stimulator module via a wire connection with the implantable stimulator module, wherein the implantable secondary module is configured to generate and send, to the implantable stimulator module via the wire connection, a biphasic information signal that is synchronized with the alternating electrical power signal.

In another aspect a method is provided. The method comprises receiving, at an implantable secondary module connected to an implantable stimulator module via a wire connection, an alternating power signal from the implantable stimulator module via the wire connection, detecting, at the implantable secondary module, one or more sound signals, digitizing the sound signals to generate digital audio data, transmitting the digital audio data from the implantable secondary module to the implantable stimulator module via the wire connection as a biphasic information signal, and monitoring the biphasic information signal with an error detector in the implantable stimulator module to detect when the biphasic information signal includes an error.

BRIEF DESCRIPTION OF THE DRAWINGS

Embodiments of the present invention are described herein in conjunction with the accompanying drawings, in which.

DETAILED DESCRIPTION

Presented herein are implantable digital communication techniques for use in implantable systems, such as implantable hearing systems. An implantable system in accordance with embodiments presented herein includes an implantable stimulator module and an implantable secondary module connected to the implantable stimulator module via a wire connection. The implantable secondary module is configured to generate and send a biphasic information signal to the implantable stimulator module via the wire connection. An error detector in the implantable stimulator module is configured to detect when the biphasic information signal includes an error. For example, the error detector is configured to detect when the biphasic information signal includes two or more consecutive negative or positive pulses.

For ease of illustration, embodiments are primarily described herein with reference to one type of implantable medical system, namely a cochlear implant, that is configured to implement the implantable digital communication techniques. However, it is to be appreciated that the techniques presented herein may be used with other implantable hearing systems (e.g., auditory brainstem stimulators, direct acoustic stimulators, bone conduction devices, etc.), with other tissue-stimulating prostheses (e.g., implantable pacemakers, defibrillators, functional electrical stimulation devices, pain relief stimulators, visual prostheses, other neural or neuromuscular stimulators, etc.), or other implantable medical systems.

Figure 1:
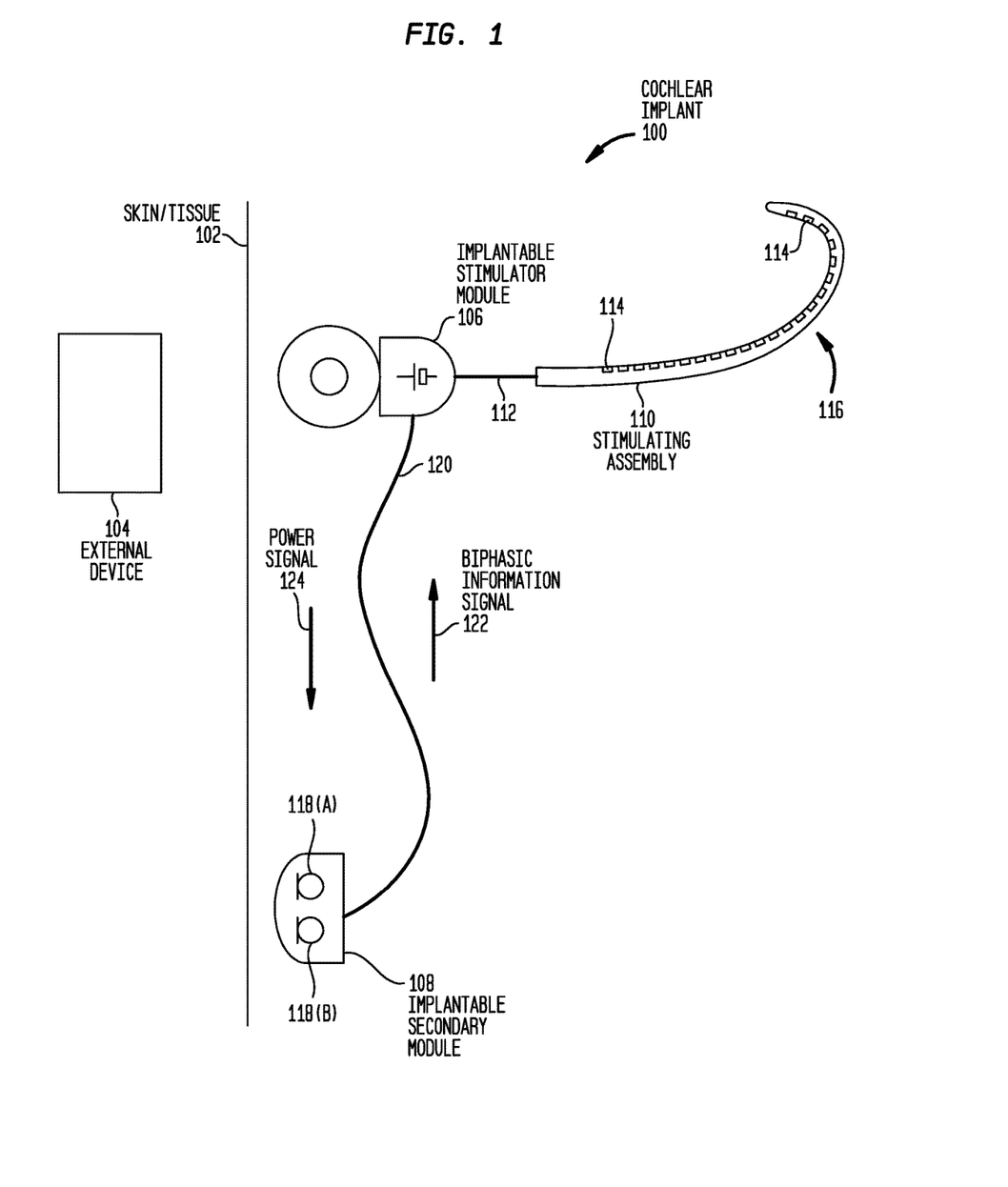
FIG. 1 is a schematic diagram of a cochlear implant that includes a digital audio link in accordance with embodiments presented herein.

FIG. 1 is a schematic diagram illustrating an exemplary totally implantable cochlear implant 100 that may be configured to implement the implantable digital communication techniques in accordance with embodiments presented herein. That is, FIG. 1 illustrates an arrangement in which all components of cochlear implant 100 are configured to be implanted under skin/tissue 102 of a recipient. Because all components of cochlear implant 100 are implantable, cochlear implant 100 operates, for at least a finite period of time, without the need of an external device. However, an external device 104 can be used to, for example, charge an implantable power source of cochlear implant 100, to supplement the performance of an implanted microphone, as a back-up power source when the implantable power source no longer functions, etc. As such, external device 104 may be a dedicated charger, a supplemental sound input element, a supplemental sound processor, etc.

Cochlear implant 100 includes an implantable stimulator module (implant body) 106, an implantable secondary module (implantable microphone module) 108, and an elongate stimulating assembly 110. The implantable stimulator module 106 has a hermetically sealed biocompatible housing in which a sound processor, power source, receiver/transceiver, stimulator components, etc. are located.

The implantable stimulator module 106 is electrically connected to a proximal end of the elongate stimulating assembly 110 via lead 112. The elongate stimulating assembly 110 is configured to be at least partially implanted in the cochlea of a recipient and includes a plurality of longitudinally spaced intra-cochlear stimulating contacts 114. The contacts 114 collectively form a contact array 116 and may comprise electrical contacts and/or optical contacts. For ease of illustration, the stimulating contacts 114 are shown as electrical contacts that deliver electrical stimulation signals (current) to the recipient.

In general, one or more components of the implantable stimulator module 106 are configured to execute sound processing and coding to convert detected sound signals into the electrical stimulation signals for delivery to the recipient via the contacts 114. In this way, cochlear implant 100 stimulates the recipient's auditory nerve cells, bypassing absent or defective hair cells that normally transduce acoustic vibrations into neural activity. In the arrangement of FIG. 1, the sound signals are provided to the implantable stimulator module 106 by implantable secondary module 108.

More specifically, the implantable secondary module 108 is electrically connected to the implantable stimulator module 106 via a wire connection provided by lead 120. The implantable secondary module 108 includes first and second sound input elements 118(A) and 118(B), respectively. The first sound input element 118(A) is, in this example, an implantable microphone (e.g., pendant microphone, tube microphone, etc.) that is configured to detect sounds for perception by the recipient. The second sound input element 118(B) is an element configured to detect body-borne sounds (e.g., eating, blood stream noises, etc.) that may be used to process/filter the desired sounds detected by the implantable microphone 118(A). For example, the second sound input element 118(B) may be an accelerometer.

As described further below, the sounds detected by the first sound input element 118(A) and the body-borne sounds detected by the second sound input element 118(B) are provided to the implantable stimulator module 106 via the lead 120. Merely for ease of description, embodiments presented herein will be described with reference to the first sound input element 118(A) as a microphone and with reference to the second sound input element 118(B) as an accelerometer. However it is to be appreciated that other sound input elements may be used in accordance with embodiments presented herein.

As noted, the sounds detected by the implantable microphone 118(A) and the body-borne sounds detected by the accelerometer 118(B) are provided to the implantable stimulator module 106 via lead 120. As described further below, the implantable stimulator module 106 is configured to deliver an alternating electrical power signal 124 to the implantable secondary module 108 via the lead 120. The power signal 124 is used to power the implantable microphone 118(A) and the accelerometer 118(B).

The wire connection provided by lead 120 may be, for example, a two-wire connection, a three-wire connection, etc. The wire connection may be susceptible to outside influences, such as alternating current (AC) leakage, direct current (DC) leakage, and/or electromagnetic interference (EMI), that may each cause data transfer errors on the lead. Such outside influences may affect the wire connection when, for example, the insulation of the lead 120 is damaged, defective, or otherwise inadequate (e.g., due to damage caused by handling, surgical operation, etc.). If the lead insulation is inadequate, it may be possible for current delivered via the stimulating contacts 114 to pass through the recipient's conductive tissue and into the wire connection. Additionally, the wire connection can be affected by EMI generated by pulsatile EM fields caused by, for example, mobile phones located in proximity to the implanted location of the cochlear implant 100, regardless of whether the insulation of lead 120 is damaged or defective. As such, the implantable digital communication techniques presented herein include an error detection system that is configured to identify interference affecting the audio link between the implantable secondary module 108 and the implantable stimulator module 106 and to initiate mitigation/corrective actions as appropriate.

More specifically, in accordance with the implantable digital communications techniques presented herein, the sounds detected by the implantable microphone 118(A) and the body-borne sounds detected by the accelerometer 118(B) are provided to the implantable stimulator module 106 as a combined biphasic information signal 122 that comprises a series of alternating positive and negative pulses. That is, the implantable secondary module is configured to generate and send a biphasic information signal 122 (i.e., a digitized signal) that represents the detected sounds. The implantable stimulator module 106 is configured to decode the received biphasic information signal 122 for use in sound processing operations and the generation of stimulation signals for delivery to the recipient. Also as described further below, the implantable stimulator module 106 includes an error detector configured to determine/detect when the biphasic information signal includes an error and mitigation components configured to initiate one or more corrective actions to mitigate the effects of the detected error.

Figure 2A:
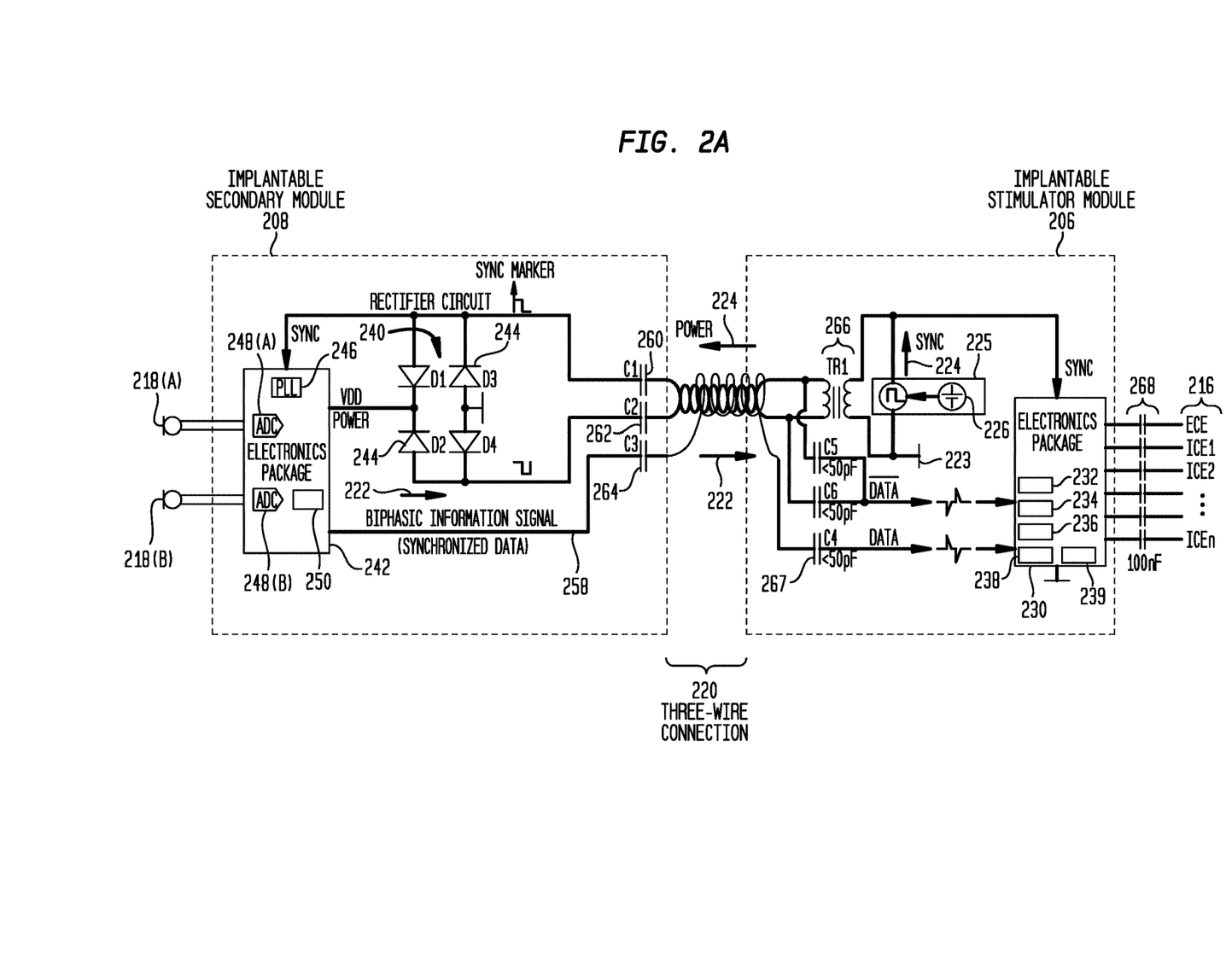
FIG. 2A is a simplified circuit diagram of a cochlear implant that includes a digital audio link and a power link in accordance with embodiments presented herein.
Figure 2B:
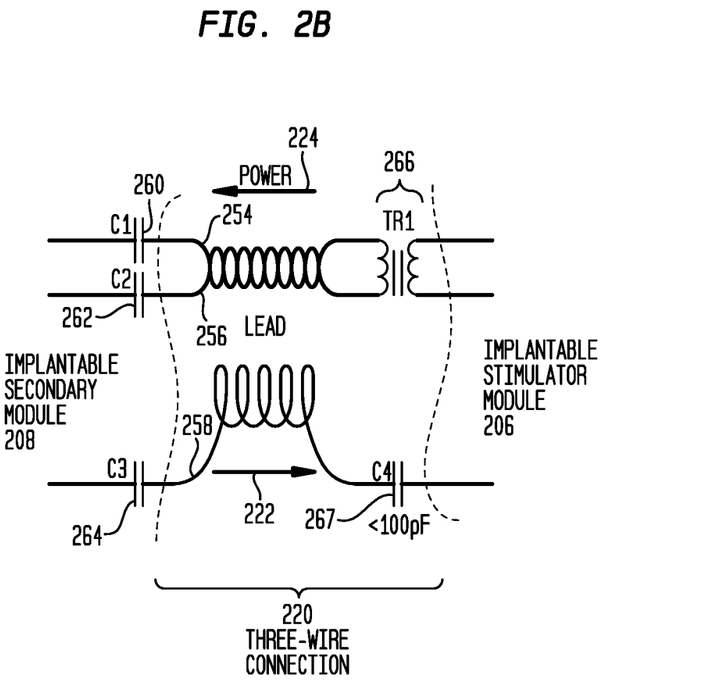
FIG. 2B is a view of a three-wire connection of the cochlear implant of FIG. 2A.

As noted above, the wire connection provided by lead 120 may be, for example, a two-wire connection, a three-wire connection, etc. FIG. 2A is a schematic diagram illustrating one embodiment of cochlear implant 100, referred to as cochlear implant 200, in which an implantable secondary module 208 is electrically connected to an implantable stimulator module 206 via a three-wire connection 220. FIG. 2B is an expanded view of the three-wire connection 220.

As shown in FIG. 2A, the implantable stimulator module 206 includes a square wave generator 225 supplied from a rechargeable power source (e.g., battery) 226 and an electronics package 230. The electronics package 230 includes, for example, a digital audio decoder 232, a sound processor 234, an error detector 236, stimulator components 238, and mitigation components 239 which, for ease of illustration, are all shown in FIG. 2A as representative blocks. In practice, the digital audio decoder 232, sound processor 234, error detector 236, stimulator components 238, and mitigation components 239 may be implemented in one or more of hardware and/or software.

The electronics package 230, and more particularly the stimulator components 238, is electrically connected to the contacts in contact array 216. The contacts in contact array 216 may comprise, for example, an extra-cochlear contact (ECE) and intra-cochlear stimulating contacts (ICES).

The implantable secondary module 208 includes a rectifier circuit 240 and an electronics package 242. The rectifier circuit 240 is formed by a plurality of diodes 244 (i.e., diodes D1, D2, D3, and D4). The electronics package 242 includes a phase-locked loop (PLL) system 246, first and second analog-to-digital (ADC) converters 248(A) and 248(B), respectively, and a biphasic information signal generator 250, each shown in FIG. 2A by representative boxes. In practice, the elements of electronics package 242 may be implemented in one or more of hardware and/or software. The electronics package 242 is connected to an implantable microphone 218(A) and an accelerometer 218(B).

In operation, the battery 226 generates an alternating electrical power signal (which is represented in FIGS. 2A and 2B by arrow 224 and referred to herein as power signal 224) that is delivered to the rectifier circuit 240 of the implantable secondary module 208 using two wires of the three-wire connection 220. As shown in FIG. 2B, wires 254 and 256 of the three-wire connection 220 are used for the transfer of the power signal 224 from the implantable stimulator module 206 to the implantable secondary module 208.

The rectifier circuit 240 extracts power from the power signal 224 and this power is provided to the electronics package 242. The implantable microphone 218(A) and the accelerometer 218(B), powered using the signals received from the implantable stimulator module 206, detect analog sound signals (e.g., desired sounds and/or body-borne sound signals). The analog sound signals detected by the implantable microphone 218(A) and/or the accelerometer 218(B) are converted into digital signals by the ADC converters 248(A) and 248(B), respectively. The electronics package 242 may also include components (not shown in FIG. 2A) that are configured to amplify and/or filter the analog signals received from the implantable microphone 218(A) and/or the accelerometer 218(B).

As noted, the electronics package 242 also includes a biphasic information signal generator 250 that is configured to generate a biphasic data/information signal that represents the sound signals detected by the implantable microphone 218(A) and/or the accelerometer 218(B). The biphasic information signal (which is represented in FIGS. 2A and 2B by arrow 222 and referred to herein as biphasic information signal 222) is synchronized with a master clock of the implantable stimulator module 206. As such, the biphasic information signal is referred to as including "synchronized data" (i.e., the audio data that is synchronized to the master clock of the implantable stimulator module 206).

For example, as shown in FIG. 2A, the power signal 224 is provided to the rectifier circuit 240 and the electronics package 242. The alternating power signal 224 is a square wave (e.g., 50% duty cycle) that operates, for example, at a frequency between 100 kilohertz (KHz) and 1 megahertz (MHz). The biphasic information signal 222 has a frequency that is a multiple of (or a fraction of) the frequency of the power signal 224, derived from the PLL system 246 inside the electronics package 242 which locks to the power signal 224. As such, the biphasic information signal generator 250 operates as combinatory logic that combines the sound signals detected at the implantable microphone 218(A) and/or the accelerometer 218(B) and transmits the data as biphasic pulses synchronized to the received power signal 224 (via the PLL system 246).

The synchronization of the frequency of the biphasic information signal 222 to the frequency of the power signal 224 facilitates decoding of the biphasic information signal 222 at the implantable stimulator module 206. The data encoded in the biphasic information signal 222 may be referred to as "raw" data in that no header or error-recovery mechanism (e.g., cyclic redundancy check (CRC)) is included.

One wire 258 of the three-wire connection 220 is used to transfer the biphasic information signal 222 from the implantable secondary module 208 to the implantable stimulator module 206. When the biphasic information signal 222 is received at the implantable stimulator module 206, the digital audio decoder 232 in the electronics package 230 decodes the incoming synchronized data embedded in the information signal. The decoded synchronized data is then used by the sound processor 234 and stimulator components 238 to generate stimulation signals for delivery to the recipient. As noted, the implantable stimulator module 206 is also configured to supply power to the implantable secondary module 208 and simultaneously provide a clock (synchronization) signal for the implantable secondary module 208.

Similar to the wire connection of FIG. 1, the three-wire connection 220 may be susceptible to outside influences, such as AC leakage, DC leakage, and/or EMI that may each cause data transfer errors. As noted above, during normal operation the biphasic information signal 222 comprises a series of alternating positive and negative pulses. In accordance with the embodiments presented herein, the error detector 236 is configured to detect when the biphasic information signal 222 includes two or more consecutive positive or negative pulses, thereby indicating that the normal operation of the audio link has been disrupted. The mitigation components 239 may be configured to take one or more corrective actions to mitigate the effect of the data transfer error and possibly determine the underlying cause of the error.

In the embodiment of FIGS. 2A and 2B, a galvanic isolation barrier is provided by DC decoupling/blocking capacitors 260 (C1), 262 (C2), and 264 (C3) and a transformer 266 housed in the implantable stimulator module 206. The transformer 266 blocks occasional AC leakages (e.g., currents emanating from the stimulating contacts). The DC blocking capacitor 267 on the data line 258 has a value that is substantially low (e.g., less than 100 picofarads (pF)) when compared to the DC blocking capacitors 268 placed in series with the stimulation contacts (e.g., 100 nanofarads (nF)). In this manner, AC leakage from the stimulating contacts into the stimulator module 206 and through the three-wire connection 220 is strongly attenuated. In certain examples, the blocking capacitors 260 and 262 may be omitted.

Figure 3:
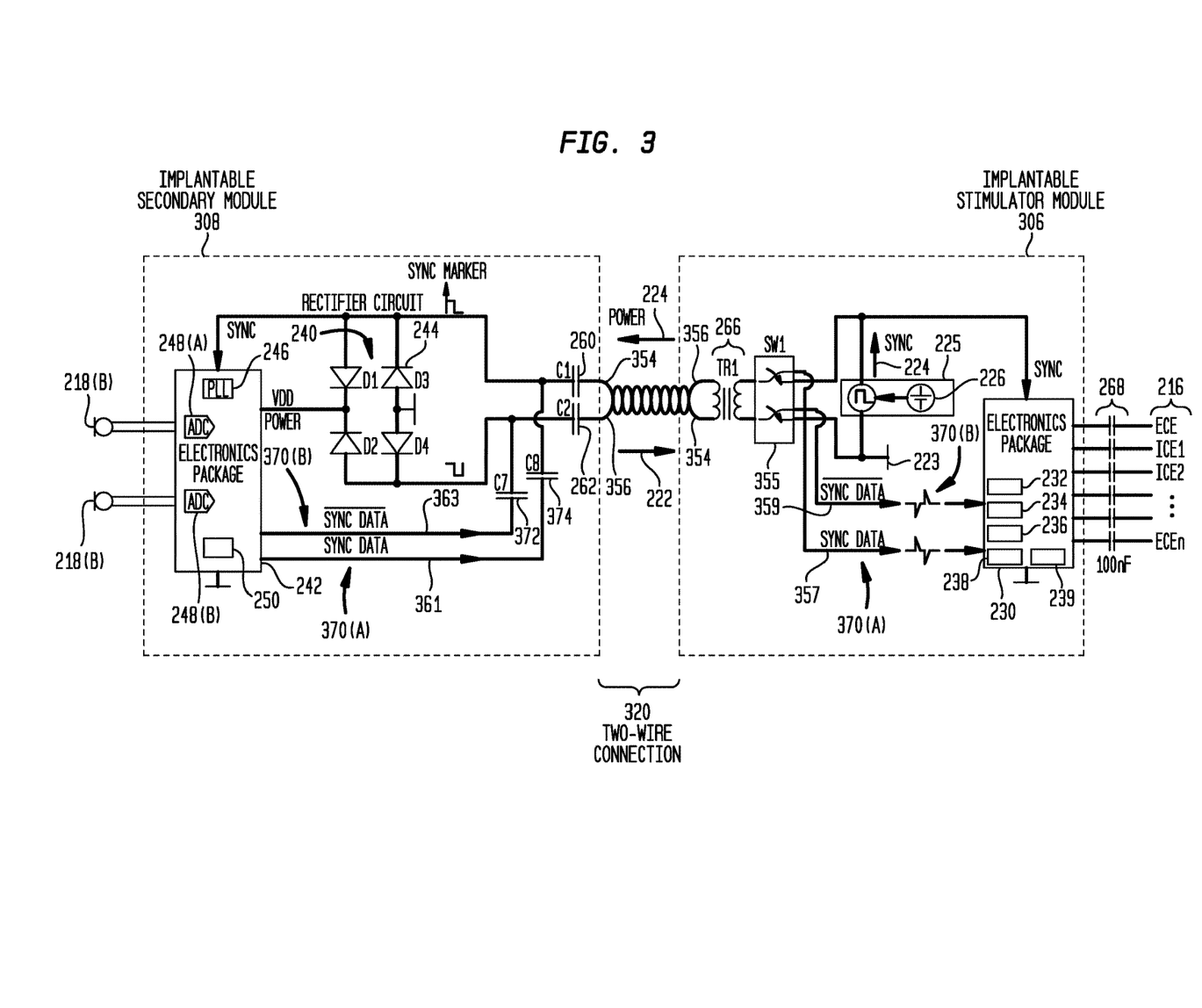
FIG. 3 is a simplified circuit diagram of a cochlear implant that includes a digital audio link and a power link in accordance with embodiments presented herein.

As noted, FIGS. 2A and 2B illustrate an embodiment in which a three-wire connection 230 is used to connect the implantable secondary module 208 to the implantable stimulator module 206. FIG. 3 is a schematic diagram illustrating an alternative embodiment for a cochlear implant 300 in which a two-wire connection 320 is used to electrically connect an implantable secondary module 308 to an implantable stimulator module 306.

The implantable stimulator module 306 and implantable secondary module 308 each have configurations that are similar to the implantable stimulator module 206 and implantable secondary module 208, respectively, of FIG. 2A. More specifically, implantable stimulator module 306 includes the rechargeable power source 226 and the electronics package 230 that comprises the digital audio decoder 232, the sound processor 234, the error detector 236, the stimulator components 238, and the mitigation components 239. The electronics package 230 of FIG. 3 is also electrically connected to the contacts in contact array 216. However, in addition to the above components, implantable stimulator module 306 also includes a switch circuit 355 that is used with the two-wire connection 320.

The implantable secondary module 308 similarly includes the rectifier circuit 240 and the electronics package 242 that comprises PLL system 246, the first and second ADC converters 248(A) and 248(B), respectively, and the biphasic information signal generator 250. The electronics package 242 is also connected to the implantable microphone 218(A) and the accelerometer 218(B).

Similar to the embodiment of FIGS. 2A and 2B, in the embodiment of FIG. 3 the battery 226 generates the alternating power signal 224 that is delivered to the rectifier circuit 240 using wires 354 and 356 of the two-wire connection 320. The rectifier circuit 240 extracts power from the power signal 224 and this power is provided to the electronics package 242. The implantable microphone 218(A) and the accelerometer 218(B), powered using the signals received from the implantable stimulator module 306, detect analog sound signals (e.g., desired sounds and/or body-borne sound signals). The analog sound signals detected by the implantable microphone 218(A) and/or the accelerometer 218(B) are converted into digital signals by the ADC converters 248(A) and 248(B), respectively. The electronics package 242 may also include components (now shown in FIG. 2A) that are configured to amplify and/or filter the analog signals received from the implantable microphone 218(A) and/or the accelerometer 218(B).

As noted, the biphasic information signal generator 250 is configured to generate the biphasic information signal 222 that represents the sound signals detected at the implantable microphone 218(A) and/or the accelerometer 218(B) and which is synchronized with a master clock of the implantable stimulator module 306. That is, the biphasic information signal 222 encodes synchronized data locked to the master clock of the implantable stimulator module 306 through PLL system 246. Also as noted, the synchronization of the frequency of the biphasic information signal 222 to the frequency of the power signal 224 facilitates decoding of the biphasic information signal 222 at the implantable stimulator module 306.

In the embodiment of FIG. 3, wires 354 and 356 of the two-wire connection 320, in addition to being used for transfer of the power signal 224, are also used to transfer the biphasic information signal 222 from the implantable secondary module 308 to the implantable stimulator module 306. More specifically, a time division multiple access (TDMA) scheme is implemented to alternate use of the two-wire connection 320 between the transfer of the power signal 224 and the biphasic information signal 222. The TDMA scheme is enabled by switch circuit 355 that alternatively connects the transformer 266: (1) between the power generator 225 and the ground 223 or (2) between signal lines 357 and 359 connected to the electronics package 230. In other words, during a first set of time slots/periods, the switch circuit 355 connects the transformer 266 between the power generator 225 and the ground 223 so as to send power signal 224 across the two-wire connection 320. However, during a second set of time slots, the switch circuit 355 connects the transformer between signal lines 357 and 359 so as receive the biphasic information signal 222 from the two-wire connection 320 and to provide the biphasic information signal 222 to the electronics package 230. As such, during the second time slots, the signal line 361 connected to the electronics package 242, the wire 356, and the signal line 357 collectively form a first data path 370(A) between the electronics package 342 and the electronics package 230. Also during the second time slots, signal line 363 connected to the electronics package 242, the wire 354, and the signal line 359 collectively form a second data path 370(B) between the electronics package 342 and the electronics package 230.

In the embodiment of FIG. 3, the biphasic information signal 222 is sent from the biphasic information signal generator 250 using differential signaling (i.e., differential mode) so as to avoid common mode interference. That is, the first data path 370(A) and the second data path 370(B) carry inverse signals (i.e., when one swings positive, the other swings negative in equal magnitude). In certain examples, the blocking capacitors 260 and 262 may be omitted.

When the biphasic information signal 222 is received at the implantable stimulator module 306, the digital audio decoder 232 in the electronics package 230 decodes the incoming synchronized data embedded in the information signal. The decoded synchronized data is then used by the sound processor 234 and stimulator components 238 to generate stimulation signals for delivery to the recipient. As noted above, the error detector 236 is configured to detect when the biphasic information signal 222 includes two or more consecutive positive or negative pulses, thereby indicating that the normal operation of the audio link has been disrupted. The mitigation components 239 may be configured to take one or more corrective actions to mitigate the effect of the data transfer error and possibly determine the underlying cause of the error.

As noted, the implantable stimulator module 306 is also configured to supply power to the implantable secondary module 308 and simultaneously provide a clock (synchronization) signal for the implantable secondary module 308. Under the TDMA scheme, during the time periods in which the PLL system 246 receives the power signal 224, the PLL system locks so as to maintain the frequency during the data slots (i.e., when the power is absent). In accordance with certain embodiments, the power and data time slots may have different lengths (e.g., short power time slots, longer audio data time slots).

In the embodiment of FIG. 3, a galvanic isolation barrier is provided by the transformer 266 housed in the implantable stimulator module 306. The transformer 266 blocks occasional AC leakages (e.g., currents emanating from the stimulating contacts). The capacitors 372 and 374 on the signal lines 363 and 361, respectively, are DC blocking capacitors to avoid DC on the signal lines.

The DC blocking capacitors 372 and 374 on the data lines 361 and 363 have values that are substantially low (e.g., less than 100 pFs) when compared to the DC blocking capacitors 268 placed in series with the stimulation contacts (e.g., 100 nFs). In certain examples, the blocking capacitors 260 and 262 may be omitted.

Merely for ease of description, further embodiments are primarily described with reference to cochlear implant 200 of FIG. 2A. However, it is to be appreciated that the embodiments presented herein may also be used in cochlear implant 300 of FIG. 3 or other implants (e.g., retina implants).

Figure 4A:
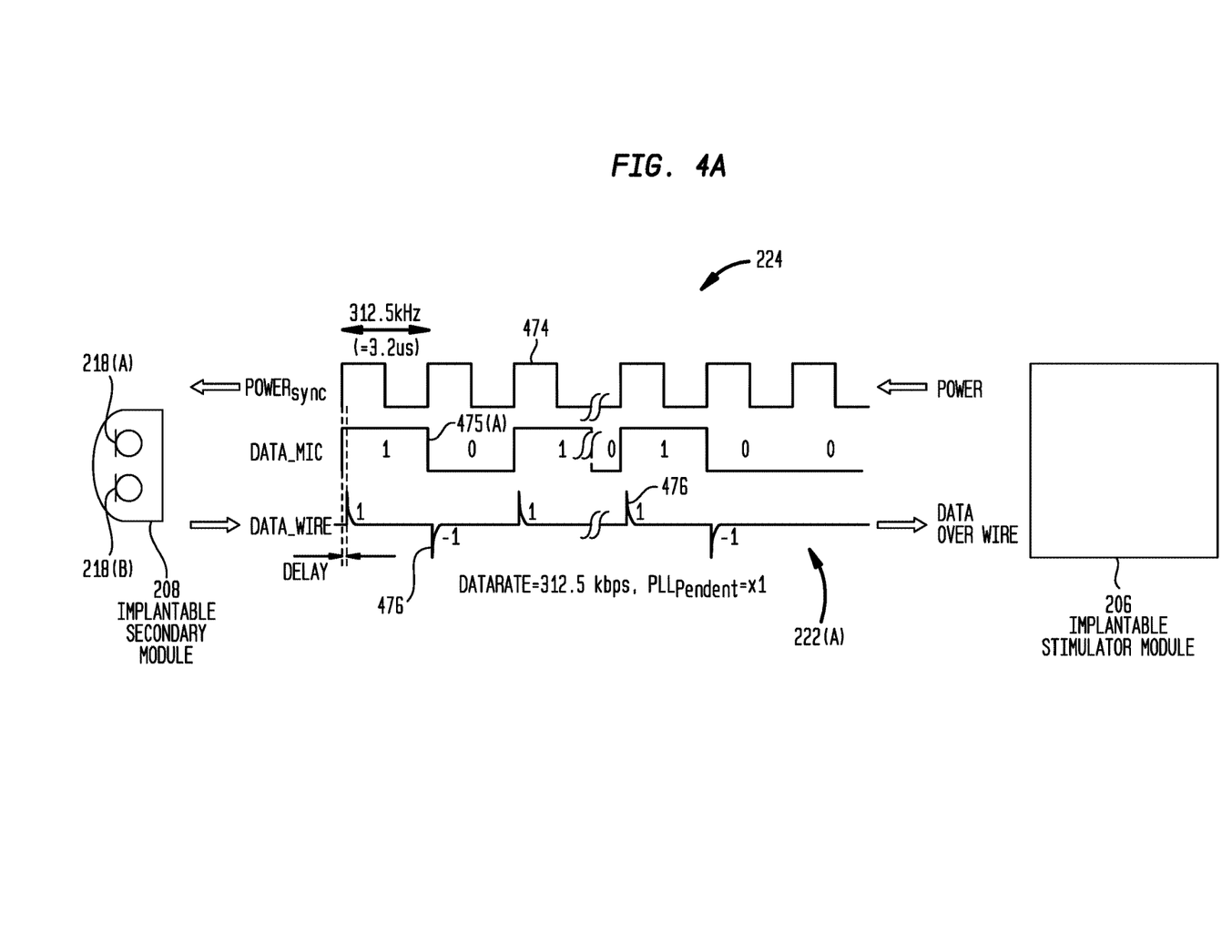
FIGS. 4A-4C are diagrams illustrating the transfer of data on a digital audio link in accordance with embodiments presented herein.

FIG. 4A is a schematic diagram illustrating the power signal 224 and an embodiment of the biphasic information signal 222, shown as biphasic information signal 222(A), that are each transferred via the three-wire connection of FIGS. 2A and 2B. As shown, the power signal 224 is a square wave with pulses 474 that each has an amplitude of VDD (e.g., 3 volts). The power signal 224 is isolated by the transformer 266 (FIG. 2A) and, in this example, the power signal has an operating frequency of approximately 312.5 KHz. The power signal 224 alternates between 0 and VDD.

The biphasic information signal 222(A) (DATA WIRE) is formed by biphasic pulses 476 that represent the rising or falling edges of the raw data stream. That is, a rising edge on the microphone data output 475(A) (DATA_MIC) (i.e., the output representing the sounds detected by implantable microphone 218(A) and the accelerometer 218(B)) results in the generation of a positive pulse and a falling edge on the data output 475(A) generates a negative pulse. During consecutive zeros and ones, there is no pulse generated and, during normal operation, every positive pulse is followed by a negative pulse and vice versa. No headers or error checking is added to the information signal 222(A) and the biphasic pulses 476 are synchronous with a multiple of the power signal 224 in order facilitate decoding of the raw data.

FIG. 4A illustrates data transfer at a data rate in which the PLL system 246 (FIG. 2A) locks to the same frequency (e.g., 312.5 KHz) as the power signal 224. That is, in the embodiment of FIG. 4A, the biphasic information signal 222(A) has substantially the same frequency as the power signal 224. However, the data transfer rate may be adjusted so as to be a multiple of, or possibly a fraction of, the power signal frequency.

Figure 4B:
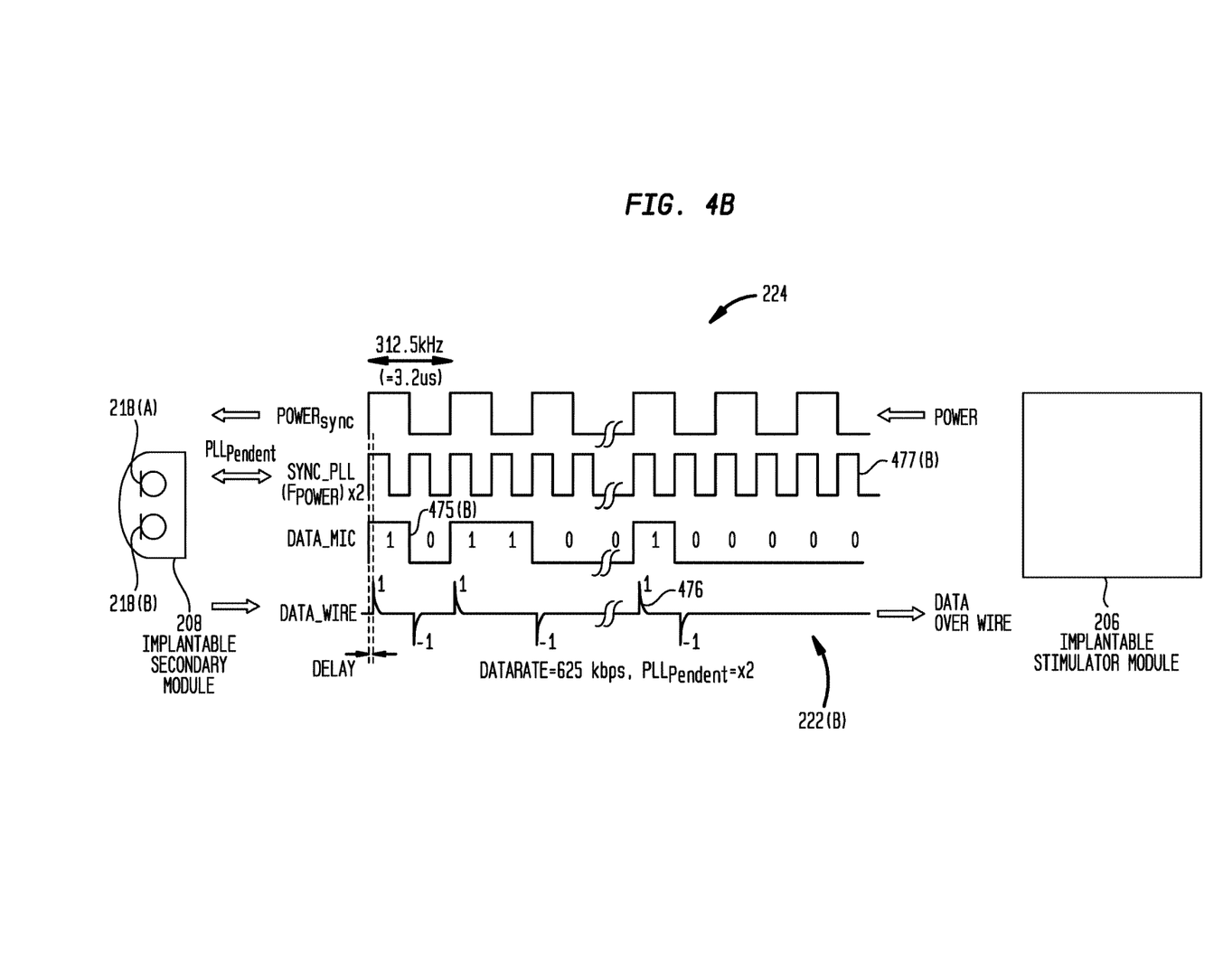

For example, FIG. 4B illustrates an embodiment that uses a data rate in which the PLL system 246 locks to twice (2×) the frequency of the power signal 224. That is, FIG. 4B illustrates that the PLL (SYNC_PLL)) signal 477(B) has a frequency of approximately 625 KHz. In this embodiment, the biphasic information signal 222(B), which is again formed by biphasic pulses 476 that represent the rising or falling edges of the raw data stream 475(B), will include twice as many pulses as that shown in FIG. 4A, thereby resulting in a data rate that is double that shown in FIG. 4A.

Figure 4C:
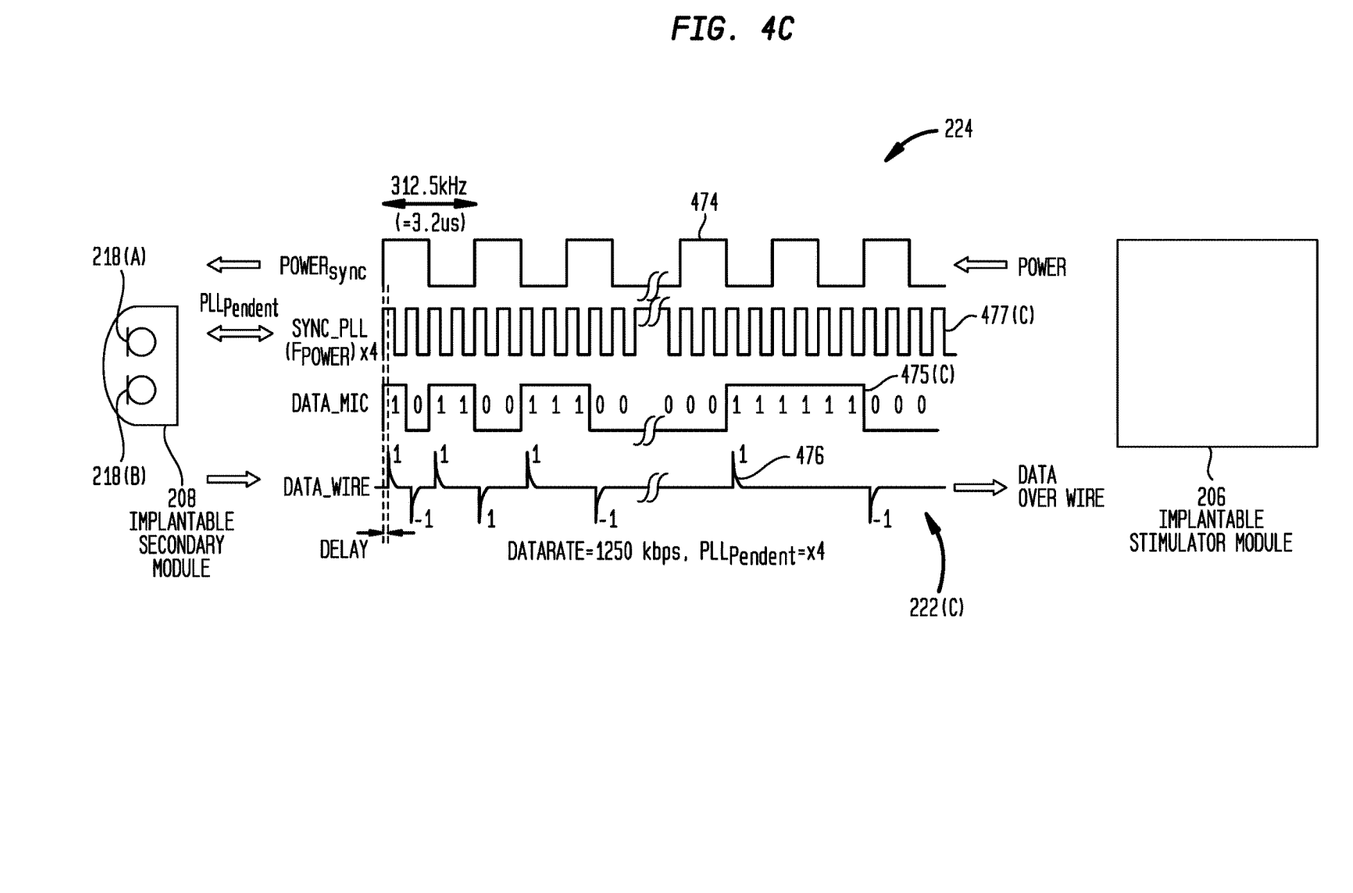

FIG. 4C illustrates another embodiment that uses a data rate in which the PLL system 246 locks to four times (4×) the frequency of the power signal 224. More specifically, FIG. 4C illustrates that the PLL signal 477(C) has a frequency of approximately 1250 KHz. In this embodiment, the biphasic information signal 222(C), which is again formed by biphasic pulses 476 that represent the rising or falling edges of the raw data stream 475(C), will include four times as many pulses as that shown in FIG. 4A, thereby resulting in a data rate that is four times that shown in FIG. 4A and twice the data rate shown in FIG. 4B.

Figure 5:
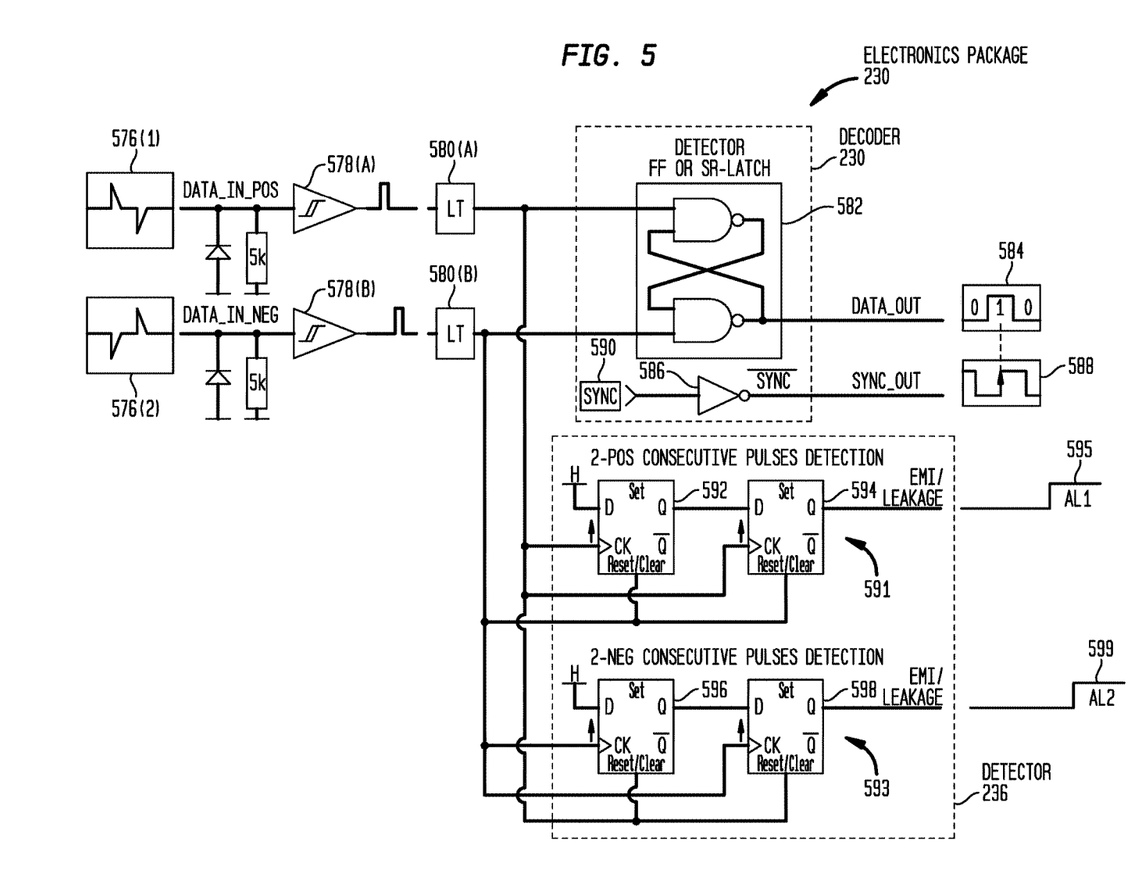
FIG. 5 is a simplified circuit diagram illustrating a digital audio decoder and an error detector in accordance with embodiments presented herein.

FIG. 5 is a simplified circuit diagram illustration a portion of the electronics package 230 of the implantable stimulator module 206 in accordance with embodiments presented herein. More particularly, FIG. 5 illustrates the digital audio decoder 230 and the error detector 236. As noted above, the digital audio decoder 230 is configured to extract the audio from the biphasic information signal 222, while the error detector 236 is configured to detect a data transfer error (i.e., when the biphasic information signal 222 includes an error).

The digital audio decoder 230 and the error detector 236 each receives positive pulses 576(1) from the wire connection 220 via a comparator/Schmitt trigger 578(A) and a level translator (LT) 580(A). Similarly, the digital audio decoder 230 and the error detector 236 each receive negative pulses 576(2) via a comparator/Schmitt trigger 578(B) and a level translator 580(B). The digital audio decoder 230 comprises a single flip-flop (FF)/set-reset (S-R) latch 582 that generates a data output (DATA_OUT) 584. The digital audio decoder 230 may include one or more inverters 586 that provide a synchronization output (SYNC_OUT) 588. The synchronization output 588 is based on a synchronization (SYNC) signal 590 derived from the master clock of the implantable stimulator module 206 (e.g., 5.011 MHz clock divided by an integer). The data output 584, synchronization output 588, and synchronization signal 590 may be provided to sound processor 234 for sound processing operations. The audio data is captured during the rising edge 588 of the inverted SYNC_OUT.

As noted, also shown in FIG. 5 is the error detector (e.g., EMI/AC leakage detector) 236 236 that is configured to detect when the biphasic information signal 222 includes two or more consecutive negative or positive pulses, thereby indicating that a data transfer of the digital audio link has occurred. The detector 236 is formed by four (4) flip-flops separated into two pairs. More specifically, a first pair 591 of flip-flops 592 and 594 are connected in series to the outputs of the level translators 580(A) and 580(B) so as to generate an output 595 (AL1) only when two consecutive positive pulses are received on the three-wire connection 220. Additionally, a second pair 593 of flip-flops 596 and 598 are connected in series to the outputs of the level translators 580(A) and 580(B) so as to generate an output 599 (AL2) only when two consecutive negative pulses are received on the three-wire connection 220. In the arrangement of FIG. 5, each pair of flip-flops 591 and 593 is a binary 2-counter counting the positive and negative pulses, respectively, and being cleared by the opposite pulse. In accordance with the techniques presented herein, two or more consecutive positive or negative pulses are a violation of the communication scheme, thus signaling a data transfer error.

Once a data transfer error has been detected, the mitigation components 239 may initiate one or more corrective actions. For example, upon the detection of an error, the mitigation components 239 could mute the audio output 584 or decrease the audio level of the audio output to protect the hearing of the recipient. Additionally, the biphasic information signal 222 is a representation of an audio signal and is divided into a plurality of discrete audio samples (e.g., 16-bit samples, 24-bit samples, etc.). If one of the samples includes an error, the mitigation components 239 may cause replacement of an audio sample that includes the error with the last received audio sample or another sample (e.g., a sample derived from earlier sample, a sample with a fixed value, etc.). Alternatively, the mitigation components 239 may instruct the implantable secondary module to attempt retransmission of a portion of the biphasic information signal 222.

In certain embodiments, the mitigation components 239 are configured to determine whether the cause of the data transfer error is EMI or current leakage. Current leakage is detected when there is some correlation between the stimulation signal and the erroneous biphasic information signal. Without such correlation, the mitigation components 239 may determine that EMI has caused the data transfer errors. When the mitigation components 239 determine that the wire connection 220 is affected by leakage, the mitigation components 239 could terminate transmission of power to the implantable secondary module 208. In certain circumstances, when the mitigation components 239 determine that the wire connection 220 is affected by contact-to-wire leakage, the mitigation components 239 could disconnect the implantable secondary module 208 or terminate transmission of power to the implantable secondary module 208.

Embodiments presented herein have been primarily described with reference to the transfer of power from the implantable stimulator module to the implantable secondary module and the transfer of data from the implantable secondary module to the implantable stimulator module. In accordance with certain embodiments, data may also be transferred from the implantable stimulator module to the implantable secondary module (i.e., in the same direction as the power and in the opposite direction of the audio data). The transmission of data from the implantable stimulator module to the implantable secondary module is sometimes referred to herein as "back-link" data transmission and the transmitted data is referred to herein as back-link data. Back-link transmissions may be used, for example, to request the microphone to convert and transfer one or more specific audio samples (e.g., when an error is detected in an previously transmitted sample) or to provide information to implantable secondary module (e.g., to change microphone settings, change time synchronization, etc.).

In accordance with certain embodiments presented herein, the back-link transmissions are enabled by extending the duty cycle of the power signal to transfer a "0" bit, a "1" bit, or a sequence thereof. That is, since for the power signal is an alternating signal, it is possible to "skip" a pulse or cycle and fill that skipped pulse/cycle with "1" or a "0."

Figure 6:
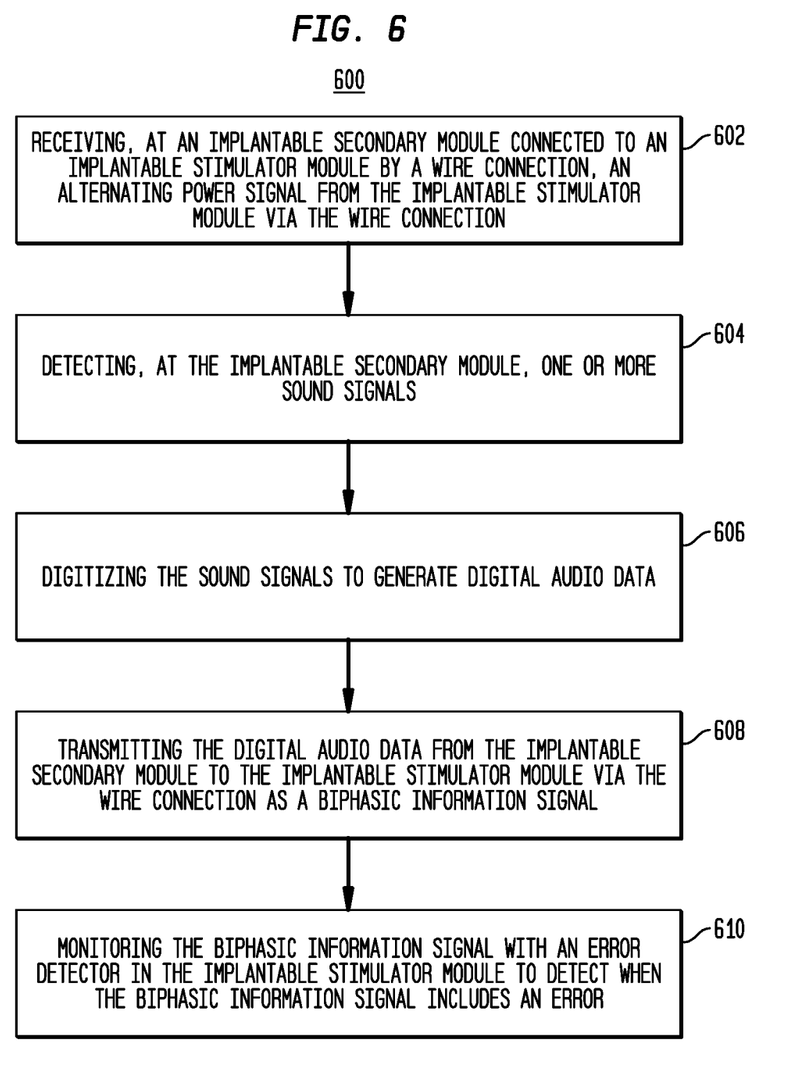
FIG. 6 is a flowchart of a method in accordance with embodiments presented herein.

FIG. 6 is a flowchart of a method 600 in accordance with embodiments presented herein. Method 600 starts at 602 where an implantable secondary module connected to an implantable stimulator module via a wire connection receives an alternating power signal from the implantable stimulator module via the wire connection. At 604, the implantable secondary module detects one or more sound signals. At 606, the sound signals are digitized to generate digital audio data. At 608, the digital audio data is transmitted from the implantable secondary module to the implantable stimulator module via the wire connection as a biphasic information signal. At 610, the biphasic information signal is monitored with an error detector in the implantable stimulator module to detect when the biphasic information signal includes an error.

Although embodiments have been described herein with reference to a specific digital protocol that makes use of biphasic pulses, it is to be appreciated that other protocols may be used in further embodiments.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. An implantable medical system, comprising:
   an implantable stimulator module;
   an implantable secondary module connected to the implantable stimulator module by a wire connection, wherein the implantable secondary module is configured to generate and send, to the implantable stimulator module via the wire connection, a biphasic information signal comprising a series of alternating positive and negative pulses, wherein the biphasic information signal is a digital audio signal representing detected sounds; and
   an error detector in the implantable stimulator module configured to detect when the biphasic information signal includes an error.

2. The implantable medical system of claim 1, wherein to detect an error in the biphasic information signal, the error detector is configured to detect when the biphasic information signal includes two or more consecutive negative or positive pulses.

3. The implantable medical system of claim 1, wherein the audio signal comprises raw audio with no header information.

4. The implantable medical system of claim 1, wherein when the error detector detects two or more consecutive negative or positive pulses, the implantable stimulator module is configured to:
   at least one of mute an audio output of the implantable stimulator module or decrease a level of the audio output of the implantable stimulator module.

5. The implantable medical system of claim 1, wherein when the error detector detects two or more consecutive negative or positive pulses, the implantable stimulator module is configured to replace with an erroneous sample of the audio signal with at least one of:
   a last received audio sample, a sample derived from earlier samples, or a sample with a fixed value.

6. The implantable medical system of claim 1, wherein when the error detector detects two or more consecutive negative or positive pulses, the implantable stimulator module is configured to cause the implantable secondary module to attempt retransmission of a portion of the audio signal.

7. The implantable medical system of claim 1, wherein when the error detector detects that the biphasic information signal includes two or more consecutive negative or positive pulses, the implantable stimulator module is configured to determine whether the wire connection is affected by electrical magnetic interference or current leakage.

8. The implantable medical system of claim 7, wherein when the implantable stimulator module determines that the wire connection is affected by current leakage, the implantable stimulator module is configured to terminate transmission of power to the implantable secondary module.

9. The implantable medical system of claim 1, wherein the biphasic information signal is isolated by a transformer.

10. The implantable medical system of claim 1, wherein the biphasic information signal is isolated by a capacitor.

11. An implantable medical system, comprising:
    an implantable stimulator module connected to an array of stimulation contacts to deliver stimulation signals to a recipient; and
    an implantable secondary module comprising one or more sound input elements, wherein the implantable secondary module is configured to receive an alternating electrical power signal from the implantable stimulator module via a wire connection with the implantable stimulator module, wherein the implantable secondary module is configured to generate and send, to the implantable stimulator module via the wire connection, a biphasic information signal that is synchronized with the alternating electrical power signal.

12. The implantable medical system of claim 11, further comprising:

an error detector in the implantable stimulator module configured to identify a data transfer error on the wire connection.

13. The implantable medical system of claim 12, wherein the error detector is configured to identify a data transfer error on the wire connection by detecting when the biphasic information signal includes two or more consecutive negative or positive pulses.

14. The implantable medical system of claim 12, wherein when the error detector identifies a data transfer error, the implantable stimulator module is configured to initiate one or more corrective actions.

15. The implantable medical system of claim 14, wherein to initiate one or more corrective actions, the implantable stimulator module is configured to at least one terminate delivery of stimulation signals to the recipient or decrease a level of stimulation signals delivered to the recipient.

16. The implantable medical system of claim 14, wherein to initiate one or more corrective actions the implantable stimulator module is configured to replace an erroneous sample of the biphasic information signal with a last received sample of the biphasic information signal.

17. The implantable medical system of claim 14, wherein to initiate one or more corrective actions the implantable stimulator module is configured to cause the implantable secondary module to attempt retransmission of a portion of the biphasic information signal.

18. The implantable medical system of claim 12, wherein when the error detector identifies a data transfer error, the implantable stimulator module is configured to determine whether the wire connection is affected by electrical magnetic interference or current leakage.

19. The implantable medical system of claim 11, wherein the biphasic information signal is a digital audio signal representing detected sounds.

20. An implantable medical system, comprising:

an implantable stimulator module;

an implantable secondary module connected to the implantable stimulator module by a wire connection, wherein the implantable secondary module is configured to generate and send, to the implantable stimulator module via the wire connection, a biphasic information signal comprising a series of alternating positive and negative pulses; and an error detector in the implantable stimulator module configured to detect when the biphasic information signal when the biphasic information signal includes two or more consecutive negative or positive pulses.

* * * * *

UNITED STATES PATENT AND TRADEMARK OFFICE
CERTIFICATE OF CORRECTION

PATENT NO. : 10,201,704 B2
APPLICATION NO. : 15/045582
DATED : February 12, 2019
INVENTOR(S) : Werner Meskens Page 1 of 1

It is certified that error appears in the above-identified patent and that said Letters Patent is hereby corrected as shown below:

In the Claims

Column 14, Line 27, in Claim 20, delete "when the biphasic information signal"

Signed and Sealed this
Thirtieth Day of April, 2019

Andrei Iancu
*Director of the United States Patent and Trademark Office*